(12) United States Patent
Dwivedi et al.

(10) Patent No.: US 11,069,098 B2
(45) Date of Patent: Jul. 20, 2021

(54) INTERACTIVE TARGETED ULTRAFAST RECONSTRUCTION IN EMISSION AND TRANSMISSION TOMOGRAPHY

(71) Applicant: KONINKLIJKE PHILIPS N.V., Eindhoven (NL)

(72) Inventors: Shekhar Dwivedi, Willoughby Hills, OH (US); Andriy Andreyev, Willoughby Hills, OH (US); Chuanyong Bai, Solon, OH (US); Chi-Hua Tung, Aurora, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 50 days.

(21) Appl. No.: 16/461,121

(22) PCT Filed: Nov. 22, 2017

(86) PCT No.: PCT/EP2017/079987
§ 371 (c)(1),
(2) Date: May 15, 2019

(87) PCT Pub. No.: WO2018/099772
PCT Pub. Date: Jun. 7, 2018

(65) Prior Publication Data
US 2020/0066009 A1 Feb. 27, 2020

Related U.S. Application Data

(60) Provisional application No. 62/427,173, filed on Nov. 29, 2016.

(51) Int. Cl.
*A61B 6/03* (2006.01)
*G06T 11/00* (2006.01)

(52) U.S. Cl.
CPC ............ *G06T 11/006* (2013.01); *A61B 6/032* (2013.01); *A61B 6/037* (2013.01); *G06T 2207/10104* (2013.01); *G06T 2211/424* (2013.01)

(58) Field of Classification Search
CPC ......... G06T 11/006; G06T 2207/10104; G06T 2211/124; A61B 6/032; A61B 6/037
See application file for complete search history.

(56) References Cited

U.S. PATENT DOCUMENTS 7,734,119 B2 6/2010 Cheryauka
8,903,152 B2 * 12/2014 Asma .................... G06T 11/006
382/131

(Continued)

FOREIGN PATENT DOCUMENTS

CN 104751499 A 7/2015

OTHER PUBLICATIONS

International Search Report and Written Opinion for PCT/EP2017/079987, dated Mar. 25, 2018.

(Continued)

*Primary Examiner* — Gregory M Desire

(57) ABSTRACT

An imaging data set (22) comprising detected counts along lines of response (LORs) is reconstructed (24) to generate a full-volume image at a standard resolution. A region selection graphical user interface (GUI) (26) is provided via which a user-chosen region of interest (ROI) is defined in the full-volume image, and this is automatically adjusted by identifying an anatomical feature corresponding to the user-chosen ROI and adjusting the user-chosen ROI to improve alignment with that feature. A sub-set (32) of the counts of the imaging data set is selected (30) for reconstructing the ROI, and only the selected sub-set is reconstructed (34) to generate a ROI image (36) representing the ROI at a higher resolution than the standard resolution. A fraction of the (Continued)

sub-set of counts may be reconstructed using different reconstruction algorithms (40) to generate corresponding sample ROI images, and a reconstruction algorithm selection graphical user interface (42) employs these sample ROI images.

15 Claims, 3 Drawing Sheets

(56) References Cited

U.S. PATENT DOCUMENTS

| | | | | |
|---|---|---|---|---|
| 9,155,514 | B2* | 10/2015 | Panin | A61B 6/4417 |
| 9,474,495 | B2* | 10/2016 | Ahn | A61B 6/4417 |
| 9,569,842 | B2* | 2/2017 | Matsuura | G06T 11/006 |
| 9,990,741 | B2* | 6/2018 | Panin | A61B 6/4417 |
| 2007/0057189 | A1* | 3/2007 | Jansen | G01T 1/2985 |
| | | | | 250/363.09 |
| 2008/0135769 | A1* | 6/2008 | Rosen | G01T 1/1647 |
| | | | | 250/363.09 |
| 2009/0169082 | A1* | 7/2009 | Mizuta | G01T 1/1612 |
| | | | | 382/131 |
| 2010/0166274 | A1* | 7/2010 | Busch | A61B 6/037 |
| | | | | 382/131 |
| 2010/0266099 | A1 | 10/2010 | Busch | |
| 2012/0089015 | A1 | 4/2012 | Gagnon | |
| 2020/0066009 | A1* | 2/2020 | Dwivedi | G06T 11/006 |

OTHER PUBLICATIONS

Reader, A.J. et al "Fast Accurate Iterative Reconstruction for Low-Statistics Positron Volume Imaging", Physics in Medicine Biology, vol. 43, pp. 835-846, 1998.

Cheng, Xiaoyin et al "Direct Parametric Image Reconstruction in Reduced Parameter Space for Rapid Multi-Tracer PET Imaging", IEEE Transactions on Medical Imaging, pp. 1-15, Feb. 2015.

* cited by examiner

INTERACTIVE TARGETED ULTRAFAST RECONSTRUCTION IN EMISSION AND TRANSMISSION TOMOGRAPHY

CROSS-REFERENCE TO PRIOR APPLICATIONS

This application is the U.S. National Phase application under 35 U.S.C. §371 of International Application No. PCT/EP2017/079987, filed on Nov. 22, 2017, which claims the benefit of U.S. Provisional Patent Application No. 62/427173, filed on Nov. 29, 2016. These applications are hereby incorporated by reference herein.

FIELD

The following relates generally to the image reconstruction arts, medical imaging arts, radiology workstation arts, and related arts.

BACKGROUND

In positron emission tomography (PET), a radiopharmaceutical is administered to a patient, which is pharmacologically designed to accumulate in an organ or tissue of interest. The radiopharmaceutical emits positrons each of which rapidly annihilates in an electron-positron annihilation event that emits two oppositely directed 511 keV gamma rays. In three dimensional (3D) PET imaging, the acquired PET imaging data is comprised of counts that are detected along lines of response (LORs), connecting the involved detector elements. Each count in PET is defined by two gamma rays that are simultaneously detected (within a time window) with each gamma ray being of energy 511 keV (within an energy window). In conventional PET, it is only known (neglecting scatter and random coincidences events) that the sourcing electron-positron annihilation event is located somewhere along the LOR. In time-of-flight PET (TOF-PET), the finite time difference between the two gamma rays of the pair is used to further localize the annihilation event along the LOR, e.g. using a Gaussian or other probability distribution. In medical imaging, the dosage of radiopharmaceutical administered to the patient is low to ensure patient safety, leading to long PET imaging data acquisition times and low signal to noise ratio (SNR) for the reconstructed image.

Iterative image reconstruction is a known class of image reconstruction techniques that can be tailored to provide good quality reconstructed PET images. In typical iterative image reconstruction, an initial image is provided (which in some instances may be a uniform intensity image), and this initial image is iteratively adjusted until the image projected into data space agrees with (i.e. converges to) the acquired PET imaging data.

3D iterative reconstruction is performed for a 3D volume that is divided into image elements (voxels). Within certain limits imposed by the physical resolution of the acquired PET imaging data, a higher voxel resolution for the 3D volume produces a correspondingly higher resolution image, but usually at the cost of longer iterative image reconstruction time. In practice, reconstructing a typical large-volume PET imaging data set (e.g. encompassing an entire patient torso, or encompassing the entire head of the patient, or encompassing most or all of the patient body) at the highest physically realizable resolution can take on the order of hours.

In view of this, a common work flow entails reconstructing the entire PET imaging data set at a "standard" resolution that is lower than the highest physically realizable resolution, so as to produce a full-volume image. The standard resolution is lower than the highest physically realizable resolution, but is nonetheless high enough to produce an image that is of "medical quality", that is, of sufficiently high resolution for medical personnel to draw clinical findings from the reconstructed image. The clinician can then select a region of interest (ROI) within the full-volume image, and the selected ROI is then reconstructed using higher resolution (i.e. smaller voxels) than the standard resolution. Because only the ROI is reconstructed, this ultra-fast ROI image reconstruction can be performed at the higher resolution with an acceptable reconstruction time of a few seconds or less (as compared with hours if the entire volume is reconstructed at the higher resolution). The clinician may also select the ROI image reconstruction to employ clinician-selected image reconstruction parameters. For example, the clinician may choose to employ an in-iteration smoothing or edge-enhancing filter at a chosen parameter-controlled strength in the ROI image reconstruction.

While described with reference to PET imaging, it will be appreciated that the foregoing considerations also apply to other medical imaging modalities that have similar issues with long iterative image reconstruction times, e.g. single photon emission computed tomography (SPECT) imaging, transmission computed tomography (CT) imaging, and so forth.

The following discloses a new and improved systems and methods that address the above referenced issues, and others.

SUMMARY

In one disclosed aspect, an image processing device comprises an electronic processor, a display operatively connected with the electronic processor, and at least one non-transitory storage medium storing instructions readable and executable by the electronic processor to perform an image reconstruction process including: reconstructing an imaging data set comprising counts along respective lines of response (LORs) to generate a full-volume image at a standard resolution; selecting a region of interest (ROI) by operations including at least providing a region selection graphical user interface via which a user-chosen ROI is defined in the full-volume image; selecting a sub-set of the counts of the imaging data set for reconstructing the ROI; reconstructing only the sub-set of the counts to generate a ROI image representing the ROI at a higher resolution than the standard resolution; and displaying the ROI image on the display.

In another disclosed aspect, a non-transitory storage medium stores instructions readable and executable by an electronic processor to perform an image reconstruction process. In this process, an imaging data set comprising counts along lines of response (LORs) is reconstructed to generate a full-volume image at a standard resolution. A region of interest (ROI) is selected by operations including at least: providing a region selection graphical user interface via which a user-chosen ROI is defined in the full-volume image, and automatically adjusting the user-chosen ROI at least by identifying an anatomical feature corresponding to the user-chosen ROI in the full-volume image and adjusting the user-chosen ROI to improve alignment with the identified anatomical feature. At least a sub-set of the counts of the imaging data set is reconstructed to generate a ROI image representing the ROI at a higher resolution than the standard resolution.

In another disclosed aspect, an image reconstruction process is disclosed. An imaging data set comprising counts along lines of response (LORs) is reconstructed to generate a full-volume image at a standard resolution. A region of interest (ROI) is selected by operations including at least providing a region selection graphical user interface via which a user-chosen ROI is defined in the full-volume image. A fraction of the counts of the imaging data set is reconstructed using a plurality of different reconstruction algorithms to generate a corresponding plurality of different sample ROI images representing the ROI. A reconstruction algorithm selection graphical user interface is provided, via which a user-chosen reconstruction algorithm is selected form the plurality of different reconstruction algorithms. The reconstruction algorithm selection graphical user interface displays reconstruction algorithm selection user dialogs comprising the sample ROI images representing the ROI. At least a sub-set of the counts of the imaging data set is reconstructed using the user-chosen reconstruction algorithm to generate a ROI image representing the ROI at a higher resolution than the standard resolution. The ROI image is displayed on a display.

One advantage resides in providing improved image quality for a region of interest.

Another advantage resides in providing more efficient image reconstruction of a region of interest.

Another advantage resides in providing a user interface that guides medical personnel as to the choice of image reconstruction.

Another advantage resides in providing improved selection of a region of interest for enhanced image reconstruction.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
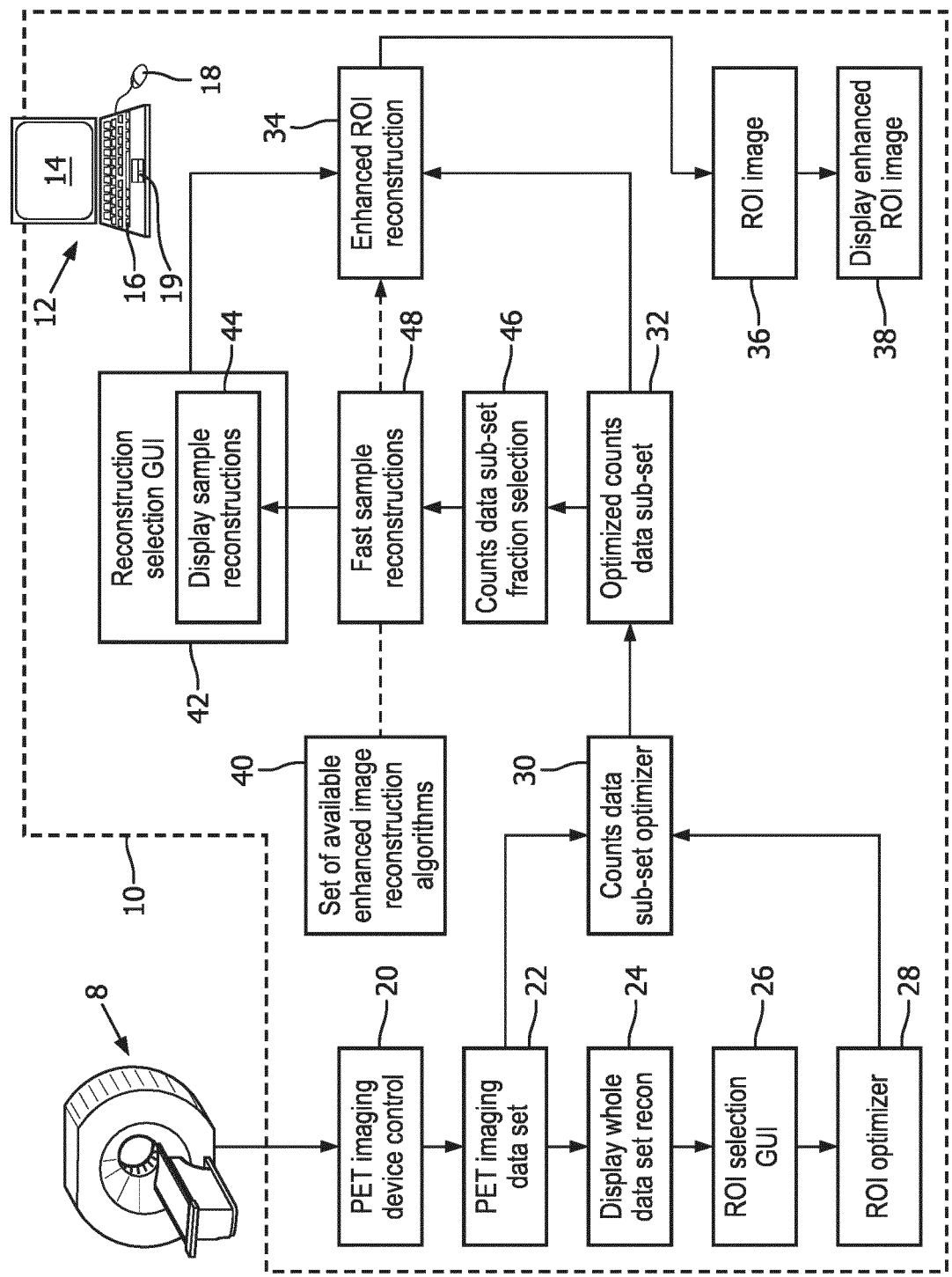
FIG. 1 diagrammatically shows an illustrative imaging device including improved image reconstruction as disclosed herein.

With reference to FIG. 1, an illustrative imaging device comprises a positron emission tomography (PET) imaging scanner 8 and an electronic processor 10 programmed to process imaging data acquired by the PET imaging scanner 8 to generate one or more reconstructed images. The PET imaging scanner 8 acquires an imaging data set comprising lines of response (LORs). The LORs may or may not include time of flight (TOF) localization. In non-TOF PET, each LOR is defined by two simultaneously detected (within a time window) gamma rays each of which has energy 511 keV (within an energy window). In TOF-PET each LOR additionally includes a spatial localization of the positron-electron annihilation event along the LOR, e.g. represented as a Gaussian distribution of width determined based on temporal resolution of the PET detectors. While the illustrative embodiment employs PET (encompassing both non-TOF and TOF PET), this is merely an illustrative example and the disclosed image processing and image processing workflow techniques are also applicable to like types of medical imaging modalities that employ iterative image reconstruction, such as single photon emission computed tomography (SPECT) imaging or transmission computed tomography (CT) imaging. In the case of SPECT imaging, the illustrated PET imaging scanner 8 is typically replaced by a gamma camera (sometimes called a nuclear camera) with one, two, three, or more movable radiation detector heads (although a detector ring is also contemplated), and the counts are lines of response (LORs) which are defined by collimators of the gamma camera used to acquire the SPECT imaging data set, e.g. honeycomb collimators. Thus, in SPECT, each count (LOR) corresponds to a single emission particle (or photon) detection event. In CT imaging, the PET imaging scanner 8 is typically replaced by a CT scanner and the counts are lines of response (LORs) which are defined by the x-ray tube-to-detector element connecting lines. By way of some non-limiting illustrative examples, the illustrative PET imaging scanner 8 may be the PET gantry of a Vereos™ Digital PET/CT scanner or an Ingenuity™ TF PET scanner, an example of a gamma camera is the Forte™ nuclear medicine camera, while an example of a CT scanner is the CT gantry of the aforementioned Vereos™ Digital PET/CT scanner. These illustrative commercial imaging scanners, and other suitable scanners, are available from Koninklijke Philips N.V., Eindhoven, the Netherlands.

The electronic processor 10 may, for example, be embodied as a computer 12 (e.g. a desktop computer, network-based server computer, a dedicated PET control computer, various combinations thereof, or so forth) that executes instructions read from one or more non-transitory electronic storage media (e.g. one or more hard drives, optical disks, solid state drives or other electronic digital storage devices, various combinations thereof, or so forth) that stores the instructions. The computer 12 includes or has operative access to at least one display 14 (e.g. an LCD display, plasma display, or so forth), and includes or has operative access to at least one user input device via which a user can input information. The illustrative user input devices include a keyboard 16 and a mouse 18, trackpad 19, touch-sensitive overlay of the display 14, and/or other pointing device. These are intended as non-limiting examples, and other user input devices are also contemplated.

The electronic processor 10 is programmed to perform control operations, i.e. PET imaging device control 20 to acquire an imaging data set 22 comprising lines of response (LORs). In an operation 24, the imaging data set 22 is reconstructed using any suitable image reconstruction algorithm to generate a full-volume image at a standard resolution which is displayed to the user on the display 14. The electronic processor 10 is further programmed to provide a region selection graphical user interface 26 via which a user-chosen region of interest (ROI) is defined in the full-volume image. This may, for example, entail displaying user-selected slices of the 3D full-volume image generated in the operation 24, so that the user can delineate the user-chosen ROI by drawing contours around the organ or other anatomical feature of interest.

In an operation 28, the user-chosen ROI is automatically adjusted, for example by identifying an anatomical feature in the full-volume image corresponding to the 3D ROI and adjusting the ROI to improve alignment of the ROI with the identified anatomical feature. Thus, for example, if the user-chosen ROI encompasses at least a threshold fraction (e.g. 80%-100% in some non-limiting embodiments) of the heart, then the operation 28 detects this and performs automated segmentation to delineate the volume containing the heart and adjusts the 3D ROI to match this volume. As another example, if the user-chosen ROI is found to encompass a threshold fraction of the prostate organ then the operation 28 detects this and performs automated segmentation to delineate the volume containing the prostate and adjusts the ROI to match this volume. Optionally, the operation 28 may add a margin such that the adjusted ROI encompasses a volume including the anatomical feature (e.g. heart or prostate) and the margin surrounding the anatomical feature. In one illustrative example suitable for TOF-PET, the margin may be chosen based on the TOF localization uncertainty (for example, the margin may be set to two times, or three times, the standard deviation of a Gaussian TOF kernel used to represent the TOF localization along the LOR). In other embodiments, the margin may be set based on a statistical uncertainty of the boundaries of the automated delineation of the anatomical feature of interest.

An advantage of some embodiments of the automated ROI adjustment operation 28 is that it can facilitate relaxation of the manual contouring requirements imposed on the clinician performing the user-chosen ROI definition via the region selection graphical user interface 26. For example, ordinarily the clinician would need to contour an anatomical feature of interest in at least two, and more preferably at least three, non-parallel planes in order to sufficiently define the ROI. In some embodiments, the clinician may contour the anatomical feature of interest in as few as a single plane, and the operation 28 then identifies the organ that is being chosen from the user-drawn contour in this single plane and proceeds to automatically segment the organ in 3D and propose the segmented organ to the clinician as the ROI for enhanced image reconstruction.

With continuing reference to FIG. 1, in an operation 30 an optimized sub-set 32 of the imaging data set 22 is selected for use in enhanced reconstruction of the ROI. The operation 30 is based on the insight herein that not all detected counts of the imaging data set 22 are likely to be relevant to reconstructing the ROI, and moreover less than the full imaging data set 22 is likely to be needed to achieve a desired enhanced reconstructed ROI image. In some embodiments, the optimized sub-set 32 of counts is reconstructed in an operation 34 using an iterative image reconstruction algorithm in order to generate a ROI image 36 representing the ROI at a higher resolution than the standard resolution at which the full-volume image was reconstructed. This ROI image 36 is suitably displayed on the display 14 in an operation 38, or is otherwise utilized. The iterative reconstruction algorithm used in the operation 34 is suitably chosen from a set of available enhanced image reconstruction algorithms 40. The plurality of different image reconstruction algorithms 40 may differ by employing different iterative reconstruction algorithms, such as an ordered subset expectation maximization (OSEM) image reconstruction algorithm, a maximum a posteriori (MAP) reconstruction algorithm, or so forth. Different reconstruction algorithms of the set of reconstruction algorithms 40 may additionally or alternatively differ by employing different parameter values for the same underlying reconstruction algorithm, and/or by employing different prior information for the same underlying reconstruction algorithm (e.g. the MAP image reconstruction algorithm using a quadratic prior is different than the MAP image reconstruction algorithm using an edge-preserving prior), and may additionally or alternatively differ by employing different image filtering. In practice, the clinician is in many circumstances not an imaging expert, and may not recognize the different capabilities of these various different image reconstruction algorithms 40. As a consequence, the clinician may select a less-than-ideal image reconstruction algorithm from the set of available enhanced image reconstruction algorithms 40 for use in the operation 34.

To address this problem, in illustrative FIG. 1 the electronic processor 10 is further programmed to provide a reconstruction selection graphical user interface (GUI) 42 to assist the clinician in selecting an optimal image reconstruction algorithm from the set of available enhanced image reconstruction algorithms 40 for use in the operation 34. The reconstruction selection GUI 42 performs an operation 44 in which efficiently reconstructed sample ROI images are displayed to assist the clinician in the selection. To this end, a LOR sub-set fraction selection operation 46 is performed to select a fraction of the sub-set 32 of the LORs, and in an operation 48 this fraction of the sub-set is reconstructed using each image reconstruction algorithm of the set of available image reconstruction algorithms 40 to generate sample reconstructions. The fraction selection is chosen to balance sufficient image quality for selection of the reconstruction algorithm against excessive reconstruction time.

Figure 2:
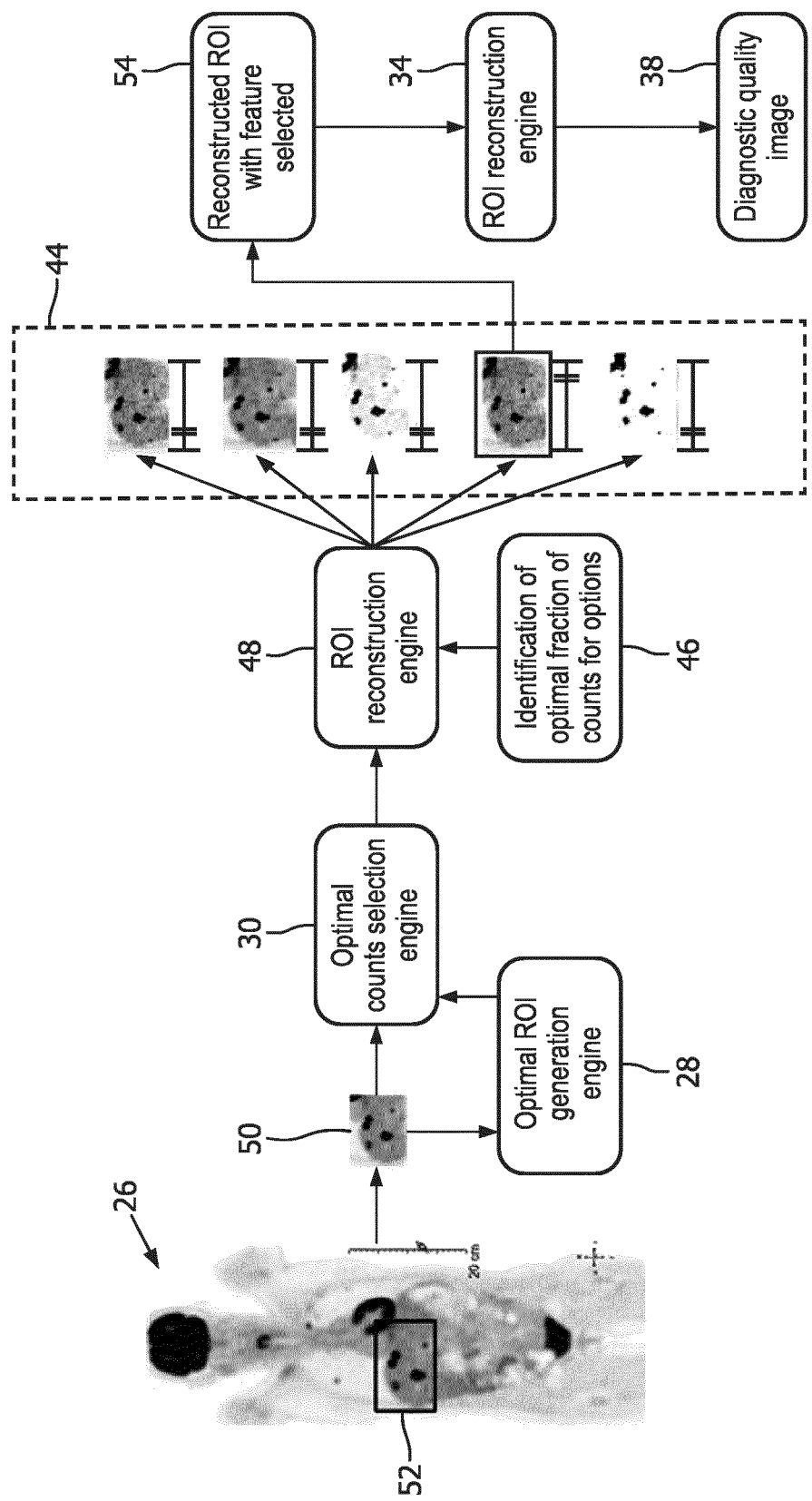
FIG. 2 diagrammatically shows an illustrative image reconstruction work flow and graphical user interface suitably executed by the imaging device of FIG. 1.

With reference to FIG. 2, an illustrative work flow example employing the imaging device of FIG. 1 is described. FIG. 2 shows a diagrammatic screen shot for an illustrative embodiment of the ROI selection GUI 26, in which the operation 24 provides the display of the full-volume image at a standard resolution, and a user-chosen ROI 50 is defined in the full-volume image, e.g. by the physician operating the mouse 18 (FIG. 1) to draw a rectangular contour 52 in the full-volume image. The physician (or other clinician) selects the ROI 50 based on free hand selection 52, contouring or the like. The ROI optimizer 28 then refines the ROI using anatomical, local and/or topological information. Refinement may include, for example, segmenting the organ or other anatomical feature of interest identified using the GUI 26 and adjusting the ROI to wholly contain this feature of interest, optionally with an additional margin. The counts data sub-set optimizer 30 then iteratively optimizes the data subset for reconstructing the ROI. This may be done, for example, using an adaptive logic to determine the number of counts to be used for enhanced reconstruction of the count-optimized ROI image. The selected data sub-set 32 is specific to the targeted ROI. In some embodiments, the ROI optimization 28 and the data sub-set optimization 30 are performed together as a combined operation. As an example, data in an ROI may come from different frames (if a step-and-shoot imaging data acquisition mode is used), and then the counts from different frames are combined. So if an organ has an overlap from two frames, but the reconstruction uses the count data from just one frame (as in a conventional frame-by-frame reconstruction) then the image quality will be reduced as compared with using all available data from both frames. To improve on this, the data sub-set optimizer 30 includes the counts from all relevant frames and then perform the reconstruction. Advanced (and optionally real time) image reconstruction of the ROI is performed using the optimized data subset 32. In some embodiments, the fraction selection 46 adaptively selects a fraction of the counts for fast real-time image reconstruction 48. To give an example, ultra-fast but relatively low quality reconstruction is obtained if, for example, 20% of the optimum LORs sub-set 32 is selected. If higher quality but slower sample reconstruction is desired, the percentage may be increased. This is done for the available reconstruction algorithms 40, and the display 44 presents options of the several ROI reconstructions to the physician. The set of available reconstruction algorithms 40 may also be pre-selected by the physician depending upon the case, e.g. a set of available reconstruction algorithms curated for use in cardiac image reconstruction may be selected in the case of a cardiac imaging task. In an operation 54, the physician operates the reconstruction selection GUI 42 of FIG. 1 to select a particular reconstruction algorithm for use in the ROI reconstruction engine 34 to generate the final diagnostic ROI image 38.

With continuing reference to FIG. 2, the reconstruction selection GUI 42 of FIG. 1 can include various features for facilitating selection of the optimal image reconstruction algorithm. For example, each fast sample reconstructed ROI image can include an associated slider 56 or other input by which the user can select to have the image quality of the sample ROI image be altered as desired. The slider (or sliders) 56 serves as a reconstruction parameter user input dialog 56 associated with each sample ROI image, and represents how the sample ROI image should be reconstructed (smoothness/sharpness, etc). User updating of the reconstruction parameters via the parameter user input dialog 56 causes the (re-)reconstructing 48 of the sub-set of the LORs using the corresponding reconstruction algorithm to generate an updated sample ROI image and displaying the updated sample ROI image. In this way, the user can perform "custom" reconstruction using the different reconstruction algorithms 40 to select the optimal reconstruction algorithm and its parameters.

With reference back to FIG. 1, the ROI selection GUI 26 is operated by the physician to select the user-chosen ROI. This ROI selection can be selected manually, e.g. by free hand drawing, or through an automatic algorithm for example, the physician can request segmentation of the heart to generate the user-chosen ROI as an automatically segmented heart volume. However, the ROI is to be defined in 3D, which is difficult for the physician to do accurately, especially when under time constraints. Doctors may also just do a free hand drawing, and may expect for accurate ROI being generated automatically. The ROI optimizer 28 then adaptively adjusts the ROI using anatomical and/or other information available to iteratively correct the ROI volume and shape. The same ROI can have different characteristic for different cases and scenarios. The optimal ROI optimizer 28 takes such inputs into consideration and generates the optimal ROI. A clinician generally wants to see details in the ROI, rather than the entire acquired patient volume. The ROI is usually only a small fraction of the full reconstructed volume (e.g. the full volume produced in operation 24). Further, all counts are not needed for reconstructing the ROI. Rather, the iterative count subset selection process 30 is performed to select an optimal subset of involved counts 32 to be used in the reconstruction process of the ROI.

Figure 3:
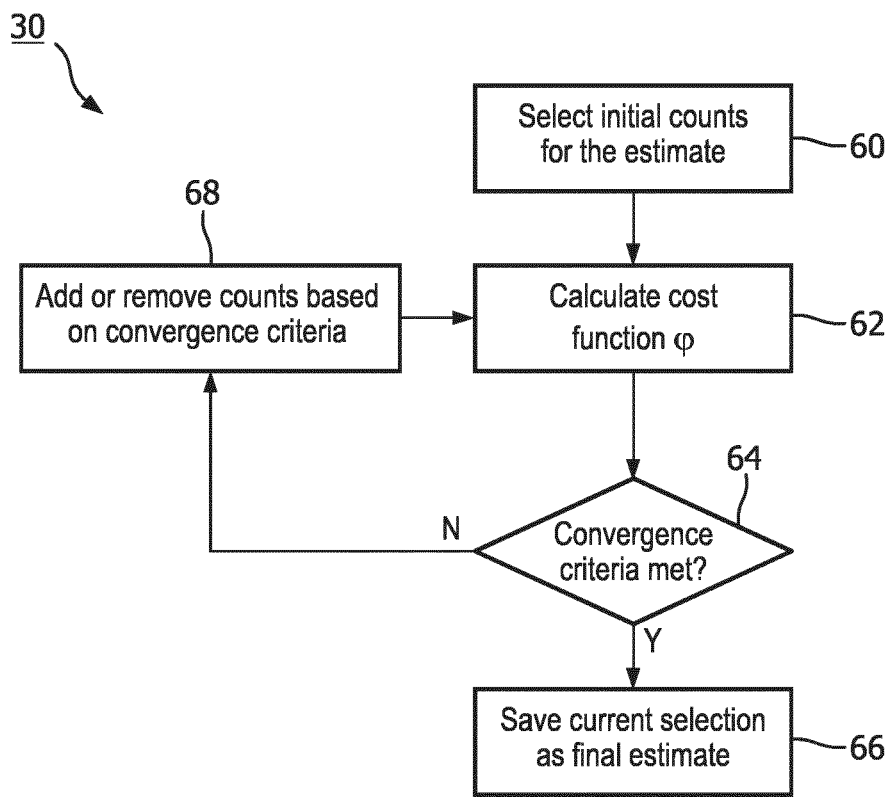
FIG. 3 diagrammatically shows a method for selecting an optimal set of counts for region of interest (ROI) reconstruction suitably performed by the imaging device of FIG. 1 executing the work flow of FIG. 2.

With continuing reference to FIG. 1 and with further reference to FIG. 3, an illustrative embodiment of the iterative detected counts subset selection process 30 is described. In an operation 60, an initial sub-set of the counts of the imaging data set 22 is selected. In some embodiments, the initial sub-set of the counts is selected to include all counts geometrically passing through the ROI. In some TOF-PET embodiments in which the counts include TOF localization, the initial sub-set of the counts is selected to include all counts having probability higher than a threshold probability that the count originated in the ROI. For example, if more than a threshold percent of the TOF probability density function lies within the ROI then it is included in the initial sub-set of counts.

In an operation 62, a cost function φ is computed. The cost function φ provides a metric of the acceptability of the image that is likely to be generated by reconstructing the chosen sub-set, balanced against computational complexity cost. The cost function used to optimize the sub-set of counts may, for example, include one or more of: a term representing the number of counts in the sub-set (e.g., penalizing the sub-set if it becomes larger than some desired target number of counts, which target number may itself be a function of the ROI size and computational power of the reconstruction engine); a term representing the TOF resolution (higher TOF resolution may enable comparable image quality and/or resolution with fewer counts, e.g. the target number of counts may also be a function of TOF resolution); desired enhanced ROI reconstructed image characteristics such as a desired resolution, contrast, or variance); and/or so forth. The cost function is used to determine whether this sub-set is acceptable. In the illustrative embodiment, iterative minimization of the cost function is performed. In an operation 64, it is checked whether the cost function is at minimum as measured by a derivative of φ. Alternatively, the operation 64 can check whether the cost function φ is below a threshold value. If the cost function is at minimum (or is below the stopping threshold value) then in an operation 66 the optimized sub-set of LORs 32 is stored for further processing. If the cost function is not at minimum (or is not below the stopping threshold value) then in an operation 68 counts are added to the initial sub-set (or, in some embodiments, counts may also be removed from the initial sub-set) and the operations 62, 64, 68 are repeated iteratively until at the operation 64 the cost function is found to be at minimum (or is determined to be below the stopping threshold value).

In some non-limiting illustrative embodiments, the set of reconstruction algorithms 40 available for reconstructing the ROI image inside the ROI, using only those counts of the sub-set 32 (e.g. those that physically intersect the ROI), are a set of iterative reconstruction OSEM-type algorithms. For this type of iterative image reconstruction algorithm, the update equation can be written in the following way (referred to herein as ROI-OSEM, where ROI refers to the region of interest being reconstructed):

$$f_{ROI,i}^{n+1,k} = \frac{f_{ROI,i}^n}{s_i + \frac{\partial U(f_i)}{\partial f_i}} \sum_j \frac{H_{ij}}{\sum_{i,m}(H_{ji}f_{ROI,i}^n + H_{jm}f_{SPEEDm}) + \text{Corr}_j}$$

In the above update equation, $f_{ROI,i}^n$—is the $n^{th}$ iteration estimate of the emission distribution inside the ROI volume (partitioned into high resolution volume elements i), $H_{ji}$ and $H_{ij}$ are the forward and backward projection operators (system matrix, may include time-of-flight and spatial resolution modelling). $H_{ij}$ is optionally adaptive and includes a suitably accurate system matrix modelling when inside the target ROI, and uses simplified system matrix when outside.

$$\frac{\partial U(f_i)}{\partial f_i}$$

is a penalty term, again to be applied only in the target ROI to speed up the computational time. $Corr_j$ are the various correction (scatter and randoms) factors and can be derived during speed optimized part, $s_i$—is the sensitivity matrix, data element index j is running over the current OSEM subset k, $f_{SPEEDm}$ is the speed optimized emission distribution estimate of the outside-ROI volume, partitioned into low-resolution volume elements m. The image $f_{SPEEDi}$ is obtained during the speed-optimized PET image reconstruction, scaled appropriately to match $f_{ROI,i}{''}$ intensity levels, is considered to be constant and is not supposed to be updated during ROI-OSEM iterations to save computational time. The product of $H_{jm}f_{SPEEDm}$ can be precomputed for each data element crossing the ROI volume and stored in memory for major computational speed improvement. Therefore, slow-speed high-resolution $H_{ji}f_{ROI,i}{''}$ operation will only be performed over limited volume of interest, saving major computational time.

The illustrative set of ROI reconstruction algorithms 40 may include various different reconstructions of the above OSEM-type. These may include at least one SUV optimized ROI image reconstruction algorithm, at least one regularized image ROI image reconstruction algorithm, at least one bilateral filter ROI image reconstruction algorithm, and/or so forth. These options are generated by operations 46, 48 and presented 44 to the physician in real time via the reconstruction selection GUI 42. In the operations 46, 48, the fraction of optimized LORs are adaptively selected to generate these options 44. For example, the sample reconstruction 48 may use X% of the optimal sub-set 32 of counts to generate an SUV optimized ROI image and Y% (which may be the same as, or different from, X%) to generate a regularized image, and so forth. Upon selection of a reconstruction algorithm by the physician via the GUI 42, the optimized subset 32 of counts determined iteratively in operation 30 are used to generate the diagnostic ROI image 36.

It should be noted that various disclosed aspects may be omitted in particular embodiments. For example, it is contemplated to include the ROI optimizer 28 but omit the count sub-set optimization 30 (in which case all counts of the imaging data set 22 are used in the ROI reconstruction) and/or omit the sample generation and display 44, 46, 48.

Likewise, it is contemplated to include the data sub-set optimization 30 but to omit the ROI optimizer 28 (in which case the user-chosen ROI is used without adjustment) and/or to omit the sample generation and display 44, 46, 48.

Likewise, it is contemplated to include the sample generation and display 44, 46, 48 but to omit the ROI optimizer 28 (in which case the user-chosen ROI is used without adjustment) and/or to omit the data sub-set optimization 30 (in which case all counts of the imaging data set 22 are used in the ROI reconstruction).

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. An image processing device comprising:
   an electronic processor;
   a display operatively connected with the electronic processor; and
   at least one non-transitory storage medium storing instructions readable and executable by the electronic processor to perform an image reconstruction process including:
   reconstructing an imaging data set comprising counts along lines of response (LORs) to generate a full-volume image at a standard resolution;
   selecting a region of interest (ROI) by operations including at least providing a region selection graphical user interface via which a user-chosen ROI is defined in the full-volume image;
   selecting a sub-set of the counts of the imaging data set for reconstructing the ROI;
   reconstructing only the sub-set of the counts to generate a ROI image representing the ROI at a higher resolution than the standard resolution; and
   displaying the ROI image on the display;
   wherein the image reconstruction process further includes:
   reconstructing a fraction of the sub-set of the detected counts using a plurality of different reconstruction algorithms to generate a corresponding plurality of different sample ROI images representing the ROI; and
   providing a reconstruction algorithm selection graphical user interface via which a user-chosen reconstruction algorithm is selected from the plurality of different reconstruction algorithms wherein the reconstruction algorithm selection graphical user interface displays reconstruction algorithm selection user dialogs comprising the sample ROI images representing the ROI;
   wherein the operation of reconstructing the sub-set of the counts to generate the ROI image representing the ROI is performed using the user-chosen reconstruction algorithm.

2. The image processing device of claim 1 wherein selecting the sub-set of the counts comprises:
   selecting an initial sub-set of the counts; and
   adding or removing counts to or from the initial sub-set to optimize a cost function.

3. The image processing device of claim 2 wherein the initial sub-set of the counts includes all counts passing through the ROI.

4. The image processing device of claim 2 wherein the counts include time-of-flight localization and the initial sub-set of the counts includes all counts having probability higher than a threshold probability that the count originated in the ROI.

5. The image processing device of claim 1 wherein the ROI is selected by the further operation of automatically adjusting the user-chosen ROI by identifying an anatomical feature corresponding to the ROI in the full-volume image and adjusting the ROI to improve alignment of the ROI with the identified anatomical feature.

6. The image processing device of claim 5 wherein automatically adjusting the ROI to improve alignment of the ROI with the identified anatomical feature includes adding a margin such that the ROI encompasses a volume including the anatomical feature and the margin surrounding the anatomical feature.

7. The image processing device of claim 1 wherein providing the reconstruction algorithm selection graphical user interface includes:
providing a reconstruction parameter user input dialog associated with each sample ROI image for receiving a value of a reconstruction parameter, wherein user updating of the value of the reconstruction parameter via the parameter user input dialog causes reconstructing the sub-set of the LORs using the corresponding reconstruction algorithm with the updated parameter value to generate an updated sample ROI image and displaying the updated sample ROI image.

8. The image processing device of claim 1 further comprising one of:
a positron emission tomography imaging device configured to acquire the imaging data set comprising counts along LORs;
a time-of-flight positron emission tomography imaging device configured to acquire the imaging data set comprising counts having TOF localization; and
a single photon emission computed tomography imaging device configured to acquire the imaging data set comprising counts defined by collimators of a gamma camera used to acquire the SPECT imaging data set.

9. A non-transitory storage medium storing instructions readable and executable by an electronic processor to perform an image reconstruction process including:
reconstructing an imaging data set) comprising counts along lines of response to generate a full-volume image at a standard resolution;
selecting a region of interest (ROI) by operations including at least:
providing a region selection graphical user interface via which a user-chosen ROI is defined in the full-volume image, and
automatically adjusting the user-chosen ROI at least by identifying an anatomical feature corresponding to the user-chosen ROI in the full-volume image and adjusting the user-chosen ROI to improve alignment with the identified anatomical feature; and
reconstructing at least a sub-set of the counts of the imaging data set to generate a ROI image representing the ROI at a higher resolution than the standard resolution;
wherein the image reconstruction process further includes:
reconstructing a fraction of the counts of the imaging data set using a plurality of different reconstruction algorithms to generate a corresponding plurality of different sample ROI images representing the ROI; and
providing a reconstruction algorithm selection graphical user interface via which a user-chosen reconstruction algorithm is selected from the plurality of different reconstruction algorithms wherein the reconstruction algorithm selection graphical user interface displays reconstruction algorithm selection user dialogs comprising the sample ROI images representing the ROI;
wherein the operation of reconstructing at least the sub-set of the counts to generate the ROI image representing the ROI is performed using the user-chosen reconstruction algorithm.

10. The non-transitory storage medium of claim 9 wherein automatically adjusting the user-chosen ROI to improve alignment with the identified anatomical feature includes adding a margin such that the ROI encompasses a volume including the anatomical feature and the margin surrounding the anatomical feature.

11. The non-transitory storage medium of claim 9 wherein the image reconstruction process further includes:
selecting a sub-set of the counts of the imaging data set for reconstructing the ROI;
wherein only the selected sub-set of the counts of the imaging data set is reconstructed to generate the ROI image representing the ROI.

12. The non-transitory storage medium of claim 11 wherein selecting the sub-set of the counts comprises:
selecting an initial sub-set of the counts; and
adding LORs to the initial sub-set or removing counts from the initial sub-set to optimize a cost function.

13. The non-transitory storage medium of claim 12 wherein the initial sub-set of the counts includes all counts passing through the ROI.

14. The non-transitory storage medium of claim 12 wherein the counts include time-of-flight localization and the initial sub-set of the counts includes all counts having probability higher than a threshold probability that the count originated in the ROI.

15. The non-transitory storage medium of claim 9 wherein providing the reconstruction algorithm selection graphical user interface includes:
providing a fraction user input dialog associated with each sample ROI image representing the fraction of the counts of the imaging data set reconstructed to generate the sample ROI image wherein user updating of the fraction via the fraction user input dialog causes reconstructing the updated fraction of the counts of the imaging data set using the corresponding reconstruction algorithm to generate an updated sample ROI image and displaying the updated sample ROI image.

* * * * *